United States Patent
Hassall et al.

[11] Patent Number: 5,770,107
[45] Date of Patent: Jun. 23, 1998

[54] REACTIVE LIQUID CRYSTALLINE COMPOUND

[75] Inventors: Ian Hassall; Simon Greenfield; David Coates, all of Dorset, Great Britain

[73] Assignee: Merck Patent Gesellschaft Mit Beschrankter Haftung, Germany

[21] Appl. No.: 725,511

[22] Filed: Oct. 4, 1996

[30] Foreign Application Priority Data

Oct. 5, 1995 [EP] European Pat. Off. .............. 95115697

[51] Int. Cl.$^6$ ..................... C09K 19/12; C09K 19/20; C09K 19/06
[52] U.S. Cl. ................. 252/299.6; 252/299.63; 252/299.66; 252/299.67; 549/562
[58] Field of Search ........... 252/299.01, 299.63, 252/299.66, 299.67, 299.6; 549/562

[56] References Cited

U.S. PATENT DOCUMENTS

| | | | |
|---|---|---|---|
| 5,204,785 | 4/1993 | Hefner, Jr. et al. | 252/299.01 |
| 5,538,768 | 7/1996 | Marden et al. | 428/1 |
| 5,543,075 | 8/1996 | Parri et al. | 252/299.01 |
| 5,622,648 | 4/1997 | Parri et al. | 252/299.66 |

FOREIGN PATENT DOCUMENTS

| | | |
|---|---|---|
| 397263 | 11/1990 | European Pat. Off. . |
| 428 213 | 11/1990 | European Pat. Off. . |
| 423 881 | 4/1991 | European Pat. Off. . |
| 606 940 | 1/1994 | European Pat. Off. . |

OTHER PUBLICATIONS

Guglielminetti et al., Polymer Bulletin 16, 411–418 (1986).
Whitcombe et al., Cinnamate Ester containing Liquid Crystalline Side Chain Polymers, J. Pol. Sci. Polym. Chem., 29, 251–259 (1991).
Singh et al., Abstract. 1993.
Kock et al., Abstract. 1989.
Tedejor et al., Syntheses and characterization of two isomeric liquid crystal series with reactive double bonds, Liq. Crys., 1993 vol. 15, No. 5, 689–700, Jan. 1993.

*Primary Examiner*—C. H. Kelly
*Attorney, Agent, or Firm*—Millen, White, Zelano & Branigan, P.C.

[57] ABSTRACT

Compounds of the formula I are useful reactive liquid crystal compounds, and can be used in a polymerizable mesogenic mixture, which can be polymerized to an anisotropic polymer. They can be used for the preparation of linear or crosslinked polymers or polymer films for decorative pigments, cosmetics, security applications, active and passive optical elements such as polarizers or retardation films, color filters, scattering displays, adhesives or synthetic resins with anisotropic mechanical properties.

11 Claims, No Drawings

REACTIVE LIQUID CRYSTALLINE COMPOUND

The invention relates to a reactive liquid crystalline compound of formula I

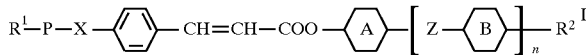

wherein
R$^1$ is CH$_2$=CW—COO—,

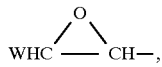

HWN—, CH$_2$=CH— or HS— CH$_2$—(CH$_2$)$_m$—COO— with W being H, Cl or alkyl with 1–5 C atoms and m being 1–7, P is alkylene with 1 to 12 C atoms, it being possible for one or more non adjacent CH$_2$ groups to be replaced by —O—, X is —O—, —S—, —CO—, —COO—, —OCO—, —C—C— or a single bond, R$^2$ is an optionally fluorinated alkyl radical with 1 to 15 C atoms, it being possible for one or more CH$_2$ groups to be replaced by —O—, —S—, —CO—, —COO—, —OCO—, —O—CO—O— in such a manner that oxygen atoms are not linked directly to one another, or alternatively R$^2$ is halogen, cyano or has independently one of the meanings given for R$^1$—P—X—, Z is —CH$_2$—CH$_2$—, —COO—, —O—CO—, —CH=CH—COO—, —O—CO—CH=CH— or a single bond,

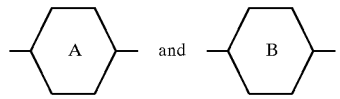

each independently denote 1,4-phenylene or trans-1,4-cyclohexylene, it being possible for these rings to be substituted by one or more alkyl, alkoxy or alkanoyl radicals with 1 to 7 C atoms, —CN, nitro or halogen atoms, and
n is 0 or 1.

The invention furthermore relates to the preparation of such compounds, to polymers or copolymers obtainable therefrom and to their applications.

Upon further study of the specification and appended claims, further objects and advantages of this invention will become apparent to those skilled in the art.

Reactive liquid crystal compounds can be polymerized in situ while in their liquid crystal phase to give anisotropic polymer films which can be used, for example, as polarizing beam splitters (like, e.g., in EP 0 428 213). Reactive liquid crystal compounds have furthermore been proposed for electrooptical scattering systems, cholesteric polarizers (like, e.g., in EP 0 606 940) and for compensation films for STN displays (like, e.g., in EP 0 428 881).

A serious drawback of the reactive liquid crystalline compounds of prior art is that they often have a low clearing temperature and a narrow mesophase range. Furthermore, the compounds of prior art often show limited values of the birefringence, which is a disadvantage in particular for the applications in optical films as described above. Consequently, there has been a considerable demand for reactive liquid crystalline compounds which exhibit alone or in mixture with other reactive liquid crystal compounds broad liquid crystal, preferably nematic or cholesteric, phase ranges with high clearing temperatures, and have a high birefringence.

One of the aims of the present invention was to provide a reactive liquid crystalline compound having these properties. Another aim of the invention was to extend the pool of reactive liquid crystalline compounds available to the expert. Other aims of the present invention are immediately evident to the person skilled in the art from the following detailed description.

It has been found that these aims can be achieved by the provision of cinnamic acid derivatives of formula I.

One object of the present invention is a reactive liquid crystalline compound of formula I

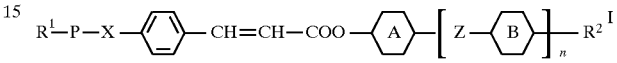

wherein
R$^1$ is CH$_2$=CW—COO—,

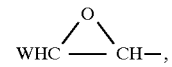

HWN—, CH$_2$=CH— or HS—CH$_2$—(CH$_2$)$_m$—COO— with W being H, Cl or alkyl with 1–5 C atoms and m being 1–7, P is alkylene with 1 to 12 C atoms, it being possible for one or more non adjacent CH$_2$ groups to be replaced by —O—, X is —O—, —S—, —CO—, —COO—, —OCO—, —C—C— or a single bond, R$^2$ is an optionally fluorinated alkyl radical with 1 to 15 C atoms, it being possible for one or more CH$_2$ groups to be replaced by —O—, —S—, —CO—, —COO—, —OCO—, —O—CO—O— in such a manner that oxygen atoms are not linked directly to one another, or alternatively R$^2$ is halogen, cyano or has independently one of the meanings given for R$^1$—P—X—, Z is —CH$_2$—CH$_2$—, —COO—, —O—CO—, —CH=CH—COO—, —O—CO—CH=CH— or a single bond,

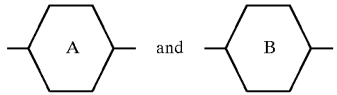

each independently denote 1,4-phenylene or trans-1,4-cyclohexylene, it being possible for these rings to be substituted by one or more alkyl, alkoxy or alkanoyl radicals with 1 to 7 C atoms, —CN, nitro or halogen atoms, and
n is 0 or 1.

In a preferred embodiment of the present invention the reactive liquid crystalline compound is a compound of formula 1, wherein n is 1 and Z is —OCO—CH=CH—.

In another preferred embodiment of the present invention the reactive liquid crystalline compound is a compound of formula 1, wherein R$^2$ has one of the meanings given for R$^1$—P—X—.

In another preferred embodiment of the present invention the reactive liquid crystalline compound is a compound of formula 1, wherein n is 0 and R$^2$ is halogen, cyano or an achiral or chiral alkyl or alkoxy group having 1 to 10 C atoms.

In yet another preferred embodiment of the present invention the reactive liquid crystalline compound is a compound of formula I, wherein at least one of the groups R$^2$ and P is a chiral group.

Another object of the present invention is a polymerizable liquid crystalline mixture comprising at least one compound of formula I as described in the foregoing and the following.

Another object of the present invention is an anisotropic polymer obtainable by polymerizing a mixture as described above.

Another object of the present invention is the use of a reactive liquid crystalline compound, a polymerizable mixture or an anisotropic polymer comprising at least one reactive liquid crystalline compound as described in the foregoing and the following for the preparation of linear or crosslinked polymers or polymer films for decorative pigments, cosmetics, security applications, active and passive optical elements such as polarizers or retardation films, color filters, scattering displays, adhesives or synthetic resins with anisotropic mechanical properties.

The inventive reactive liquid crystalline compounds are preferably selected from the following formulae wherein $R^1$, P, X and $R^2$ have the meaning given in formula I, r is 0, 1 or 2, and L is halogen, cyano, nitro or an alkyl, alkoxy or alkanoyl group with 1 to 7 C atoms.

The group

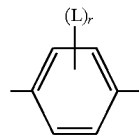

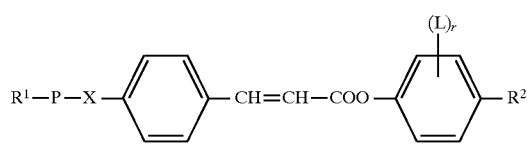

Ia

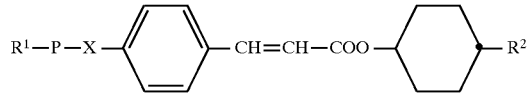

Ib

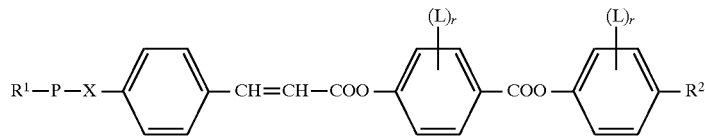

Ic

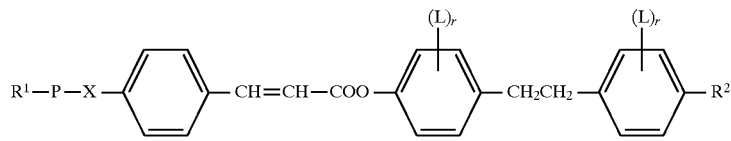

Id

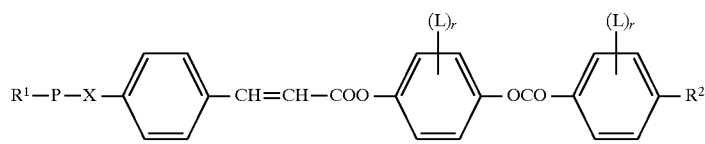

Ie

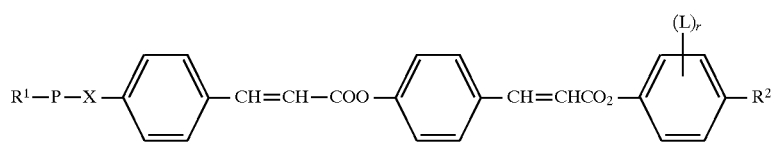

If

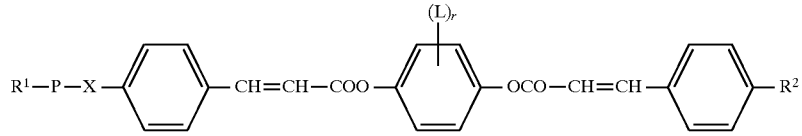

Ig

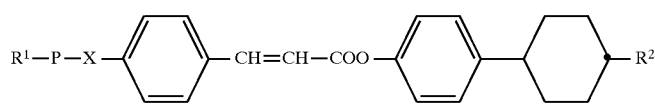

Ih

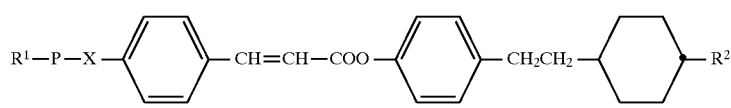

Ii in this preferred formulae particularly preferably denotes

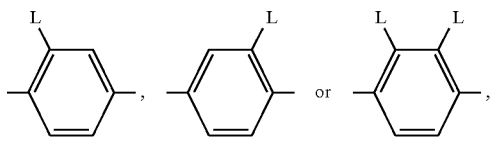

furthermore

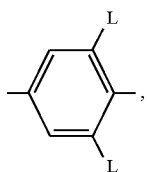

with L having each independently one of the meanings given above.

L is preferably F, Cl, CN, $NO_2$, $CH_3$, $C_2H_5$, $OCH_3$, $OC_2H_5$, $COCH_3$, $COC_2H_5$, $CF_3$, $OCF_3$, $OCHF_2$, $OC_2F_5$, in particular F, Cl, CN, $CH_3$, $C_2H_5$, $OCH_3$, $COCH_3$ and $OCF_3$, most preferably F, $CH_3$, $OCH_3$ and $COCH_3$.

$R^2$ is preferably F, Cl, CN or an alkyl or alkoxy radical with 1 to 15, preferably 1 to 10 C atoms.

If $R^2$ as given in formula I is an alkyl or alkoxy radical, i.e. where the terminal $CH_2$ group is replaced by —O—, this may be straight-chain or branched. It is preferably straight-chain, has 2, 3, 4, 5, 6, 7, 8, 9 or 10 carbon atoms and accordingly is preferably ethyl, propyl, butyl, pentyl, hexyl, heptyl, octyl, nonyl, decyl, ethoxy, propoxy, butoxy, pentoxy, hexoxy, heptoxy, octoxy, nonoxy or decoxy, furthermore methyl, undecyl, dodecyl, tridecyl, tetradecyl, pentadecyl, methoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In addition, reactive liquid crystalline compounds of the formula I containing a branched group $R^2$ can be of importance as comonomers, for example, as they reduce the tendency towards crystallization. Branched groups of this type generally do not contain more than one chain branch. Preferred branched groups are isopropyl, isobutyl (=methylpropyl), isopentyl (=3-methylbutyl), isopropoxy, 2-methylpropoxy and 3-methylbutoxy.

$R^2$ may be an achiral or a chiral group. In case of a chiral group it is preferably of the following formula

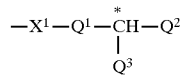

wherein $X^1$ has the meaning given for X, $Q^1$ is an alkylene or alkylene-oxy group with 1 to 7 C atoms or a single bond, $Q^2$ is an alkyl or alkoxy group with 1 to 7 C atoms which may be unsubstituted, mono- or polysubstituted by halogen or CN, it being also possible for one or more non-adjacent $CH_2$ groups to be replaced, in each case independently from one another, by by —O—, —S—, —CO—, —COO—, —OCO—, —O—CO—O— in such a manner that oxygen atoms are not linked directly to one another, or alternatively has the meaning given for $R^1$—P—X—, $Q^3$ is halogen, a cyano group or an alkyl or alkoxy group with 1 to 4 C atoms different from $Q^2$, and

* denotes the chiral carbon.

Preferred chiral groups are 2-butyl(=1-methylpropyl), 2-methylbutyl, 2-methylpentyl, 3-methylpentyl, 2-ethylhexyl, 2-propylpentyl and 2-octyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy and 2-fluorodecyloxy, for example.

In another preferred embodiment the chiral group is selected from the following groups:

a cholesteryl group,

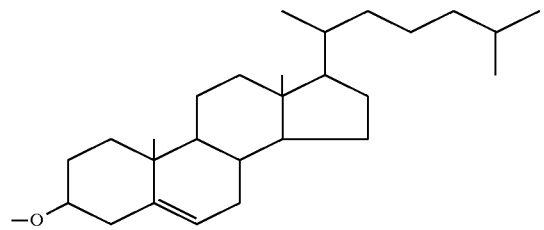

an ethylenglycol derivative

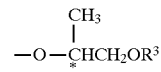

wherein $R^3$ is an alkyl radical with 1 to 12 C atoms, a terpenoid radical like, for example, menthol

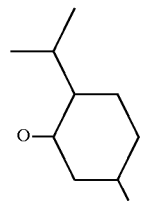

or a group based on citronellol.

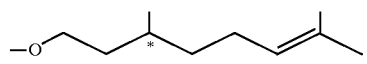

$R^1$ in formula I is preferably selected from $CH_2$=CW—COO—,

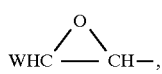

or $CH_2=CH-$ with W being H, Cl or $CH_3$.

$R^1$ is particularly preferably a vinyl group, an acrylate group, a methacrylate group or an epoxy group, very particularly preferably an acrylate or methacrylate group.

As for the spacer group P in formula I, all groups can be used that are known in the art for this purpose or analogous thereto. The spacer group P is preferably a linear or branched alkylene group having 1 to 12 C atoms, in particular 1 to 8 C atoms.

Typical spacer groups P are, for example, $-(CH_2)_o-$, $-(CH_2CH_2O)_r$ or $-CH_2CH_2-$, with o being an integer from 2 to 12 and r being an integer from 1 to 3.

Preferred spacer groups P are ethylene, propylene, butylene, pentylene, hexylene, heptylene, octylene, nonylene, decylene, undecylene, dodecylene, octadecylene, ethyleneoxyethylene, methyleneoxybutylene and 1-methylalkylene, for example.

In a preferred embodiment of the invention the spacer group is a chiral group of the formula IV:

wherein $Q^1$ and $Q^3$ have the meanings given above and $Q^4$ is an alkylene or alkylene-oxy group with 1 to 10 C atoms or a single bond, being different from $Q^1$.

In the event that R2 is a group of formula $R^1-P-X-$, the spacer groups on each side of the mesogenic core may be identical or different.

The inventive reactive liquid crystalline compounds can be prepared according to or in analogy to the following reaction schemes:

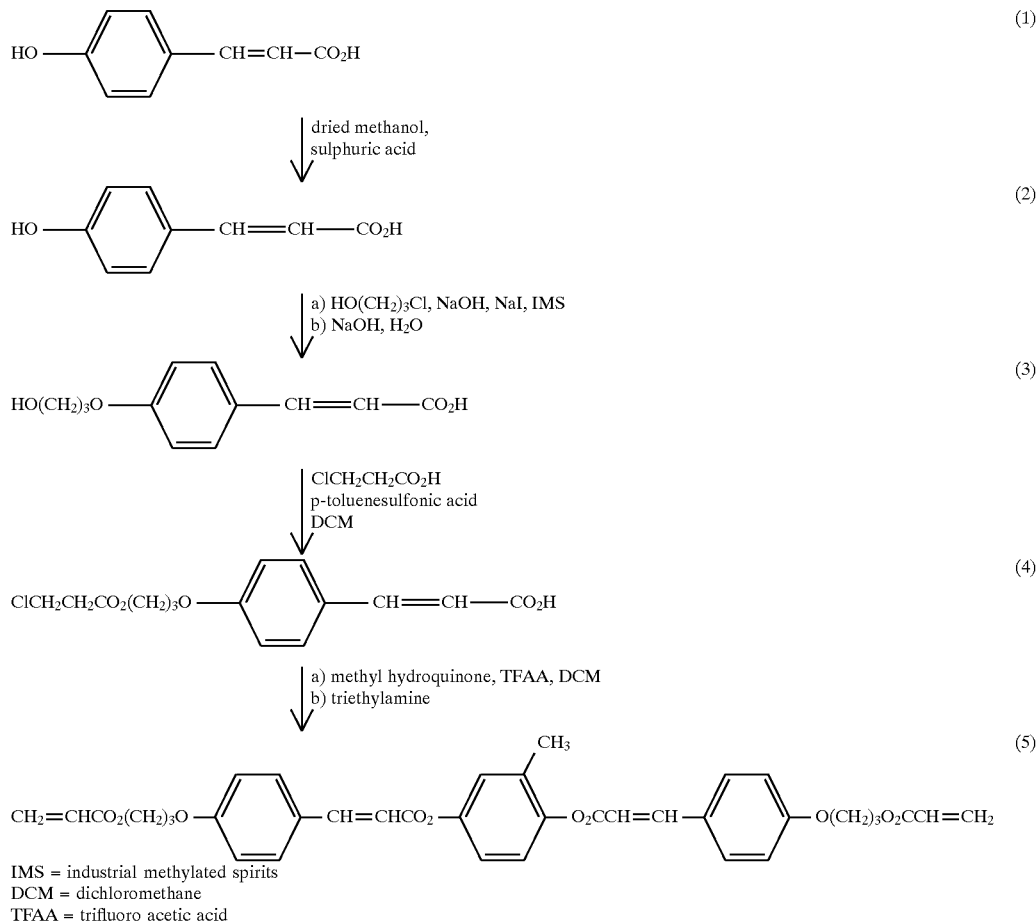

IMS = industrial methylated spirits
DCM = dichloromethane
TFAA = trifluoro acetic acid Scheme 2

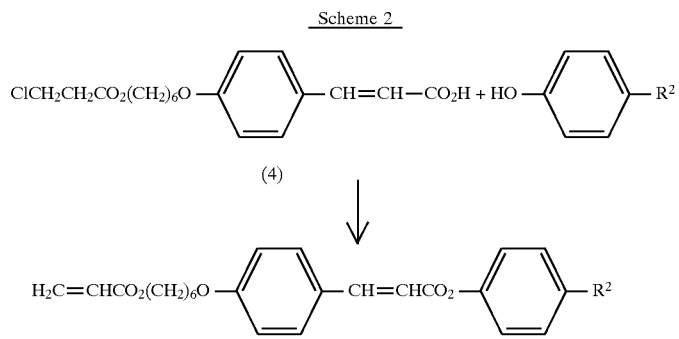

wherein $R^2$ has one of the meanings given in formula I.

Further to the methods described above, the reactive liquid crystalline compounds according to formula I can be prepared by methods which are known per se and which are described, for example, in standard works of organic chemistry such as, for example, Houben-Weyl, Methoden der organischen Chemie, Thieme-Verlag, Stuttgart.

The inventive reactive liquid crystalline compounds are characterized in that they exhibit alone or in mixture with other reactive liquid crystal compounds broad liquid crystal, preferably nematic or cholesteric, phase ranges with high clearing temperatures, and in that they have a high birefringence.

This makes these compounds especially suitable for the preparation of anisotropic polymers or polymer films that can be used as optical elements, like e.g. as polarizers, retardation films, optical waveguides or polarizing beam splitters. Another application is as polymers or polymer gels for scattering displays.

When using chiral or achiral inventive compounds in mixture together with other mesogenic compounds that may comprise chiral groups, cholesteric polymers or polymer films can be prepared. These can be used for example for cholesteric displays or in the field of decorative pigments, cosmetics or security applications.

The inventive reactive liquid crystalline compounds can easily be aligned by conventional techniques and the alignment can subsequently be frozen in by in-situ polymerization, for example by photopolymerization, to give well aligned anisotropic polymers. A detailed description of this method can be found in D. J. Broer et al., Makromol.Chem. 190, 2255 ff. (1989).

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight The following abbreviations are used to illustrate the liquid crystalline phase behaviour of the compounds:

K=crystalline; N=nematic; S=smectic; Ch=cholesteric; I=isotropic. The numbers between these symbols indicate the phase transition temperatures in degree Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding European application 95115697.5, filed Oct. 5, 1995, are hereby incorporated by reference.

EXAMPLES

Example 1

Compound (5) was prepared according to reaction scheme 1 described above.

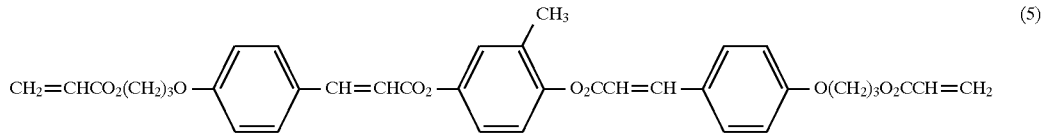

Step 1

4-hydroxy cinnamic acid (compound 1) (100 g, 0.609 moles) is refluxed overnight in dried methanol (400 mls) and sulphuric acid (50 mls). The reaction mixture is then cooled and poured in water (4 vols.) and the ester is removed by filtration to give compound 2 (94.3 g, 87%).

Step 2

Compound 2 (38 g, 0.213 moles) is refluxed overnight with 3-chloropropanol (22.17 g, 1.1 equiv.), sodium hydroxide (10.24 g, 1.2 equiv.) and sodium iodide (35.2 g, 1.1 equiv.) in IMS (400 mls). Sodium hydroxide (10.24 g, 1.2 equiv.) in water (100 mls) is then added and the mixture is again refluxed overnight The reaction mixture is then cooled and acidified. The resultant material is removed by filtration and purified by recrystallisation from ethanol to give compound 3 (40.85 g, 86%).

Step 3

Compound 3 (40.4 g, 0.182 moles) is refluxed with 3-chloropropionic acid (48.3 g, 2.5 equiv.) and p-toluene sulfonic acid (4 g, 10 wt %) in DCM (500 mls) in a reverse Dean-Stark apparatus to remove the water formed. When all has dissolved the reaction mixture is cooled, the organic layer washed free with water and run down. The material is purified by recrystallisation from IMS to give compound 4 (30.9 g, 54.3%).

Step 4

Compound 4 (2.7 g, 2.05 equiv.) is stirred at room temperature with TFM (1.24 mls, 2.08 equiv.) in DCM (50 mls). When all has dissolved, methyl hydroquinone (0.52 g, 0.0042 moles) is added as a solid and the mixture is stirred for a further 2 hours. The reaction mixture is then washed acid free with water and the organic layer is stirred overnight at 35° C. with triethylamine (5.9 mls, 10 equiv.). The reaction mixture is then cooled, washed with dil. HCl to remove excess triethylamine and the organic layer is run down. The resultant crude material is purified by recrystallisation from propan-2-ol to give compound 5 (1.2 g, 44%).

Compound 5 exhibits the mesophase behavior K 73.3N 202 and polymerizes upon heating above 202° C.

The following compound 6 was similarly prepared:

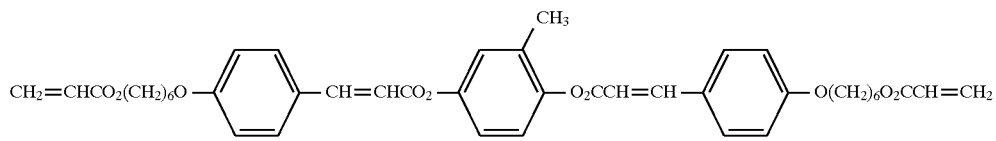

(6)

Compound 6 exhibits the mesophase behavior K 96.6N 176 I.

| No. | n | R | mesophase behaviour |
|---|---|---|---|
| 10 | 6 | OCH$_3$ | K 62.4 (S$_A$ 61) N 90 l |
| 11 | 6 | CN | K 73.9 N 98.2 l |
| 12 | 6 | C$_6$H$_{13}$ | K 38.8 S$_B$ 45.5 S$_A$ 73.3 N 75.6 l |
| 13 | 3 | Cl | K 94.0 (N 70.7) l |
| 14 | 3 | OCH$_3$ | K 82.1 (S$_A$ 34.0) N 92.2 l |
| 15 | 3 | CN | K 87.7 N 108.1 l |
| 16 | 3 | C$_6$H$_{13}$ | K 94.0 (N 70.0) l |

(2MB = 2-methylbutyl)

Comparison example

The improved mesophase behavior of the inventive compounds can be seen when comparing inventive compounds with corresponding compounds of the state of the art that contain a benzoic acid group instead of a cinnamic acid group.

|  | X = —CH=CH— (inventive compounds) | X = single bond (prior art compounds) |
|---|---|---|
| n = 3 | K 73.7 N 202 (polymerizes) | K 66 N 127 l |
| n = 6 | K 96.6 N 176 l | K 87.6 N 117.9 l |

Example 2

Compounds 7 to 16 were prepared according to reaction scheme 2 by reacting compound 4 with the respective phenol (R$^2$=2-methylbutyl, —Cl, —OCH$_3$, —CN and —C$_6$H$_{13}$ respectively).

| No. | n | R | mesophase behaviour |
|---|---|---|---|
| 7 | 3 | 2 MB | K 103.7 l |
| 8 | 6 | 2 MB | K 61.1 (S$_A$ 44 Ch 54) l |
| 9 | 6 | Cl | K 64.9 (S$_A$ 55) N 75.5 l |

|  | X = —CH=CH— (inventive compounds) | X = single bond (prior art compounds) |
|---|---|---|
| n = 6, R = Cl | K 64.9 (S$_A$ 55) N 75.5 l<br>Δn = 0.2065 | K 56.5 l<br>Δn = 0.1318 |
| n = 6, R = CN | K 73.9 N 98.2 l<br>Δn = 0.2345 | K 75.8 (N 53) l<br>Δn = 0.15947 |

(2MB = 2-methylbutyl)

When compared to the prior art compounds, in the inventive compounds the clearing point is in all cases drastically increased, whereas the melting point is only slightly increased or even reduced, thus leading to a significantly broader mesophase range.

In some cases, like e.g. for the compounds 9 (R=Cl) and 11 (R=CN), the inventive compounds show an enantiotropic nematic phase, whereas the corresponding prior art compounds exhibit no mesophase at all (R=Cl) or only a monotropic nematic phase (R=CN).

Furthermore, the inventive compounds, like e.g. compounds 9 and 11, show a significantly increased birefringence compared to the corresponding compounds of prior art.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A reactive liquid crystalline compound of formula I

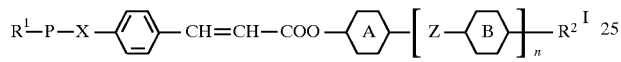

wherein

R$^1$ is CH$_2$=CW—COO—,

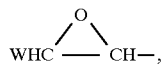

HWN—, CH$_2$=CH$_2$— or HS—CH$_2$—(CH$_2$)$_m$—COO— with W being H, Cl or alkyl with 1–5 C atoms and m being 1–7, P is alkylene with 1 to 12 C atoms, one or more non-adjacent CH$_2$ groups optionally being replaced by —O—, X is —O—, —S—, —CO—, —COO—, —OCO—, —C≡C— or a single bond, R$^2$ is an optionally fluorinated alkyl radical with 1 to 15 C atoms, one or more CH$_2$ groups optionally being replaced by —O—, —S—, —CO—, —COO—, —OCO— or —O—CO—O— in such a manner that oxygen atoms are not linked directly to one another, or alternatively R$^2$ is halogen, cyano or has independently one of the meanings given for R$^1$—P—X—, Z is —CH$_2$—CH$_2$—, —COO—, —O—CO—, —CH=CH—COO—, —O—CO—CH=CH— or a single bond,

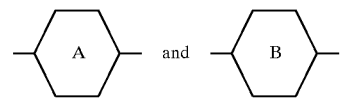

are each independently 1,4-phenylene or trans-1,4-cyclohexylene, the rings optionally being substituted by one or more alkyl, alkoxy or alkanoyl radicals with 1 to 7 C atoms, —CN, nitro or halogen atoms, and n is 0 or 1, excluding compounds of the following formula

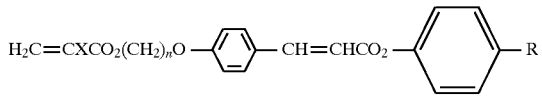

wherein X is H, Cl or CH$_3$, n is 2–12 and R is cyano or alkoxy.

2. A reactive liquid crystalline compound according to claim 1, wherein n is 1 and Z is —OCO—CH=CH—.

3. A reactive liquid crystalline compound according to claim 1, wherein n is 0 and R$^2$ is halogen, cyano or an achiral or chiral alkyl or alkoxy group having 1 to 10 C atoms.

4. A reactive liquid crystalline compound according to claim 1 selected from the following formulae

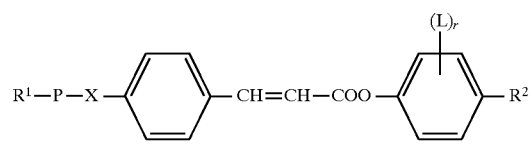

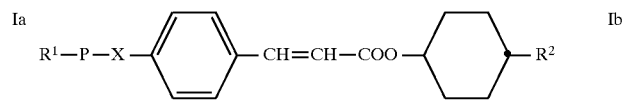

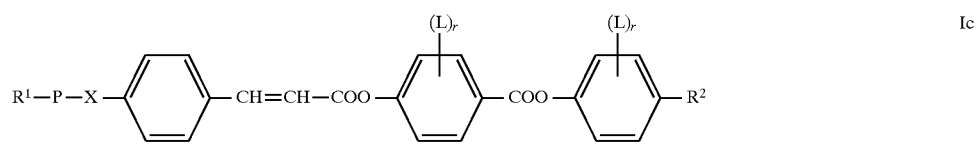

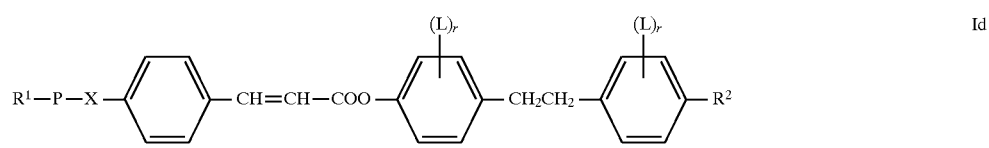

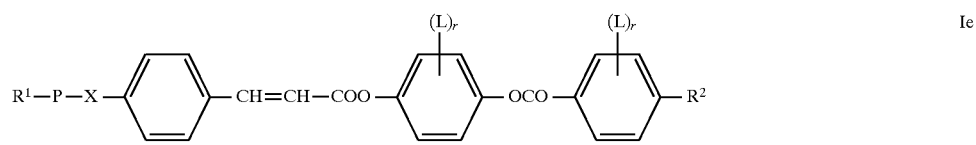

-continued

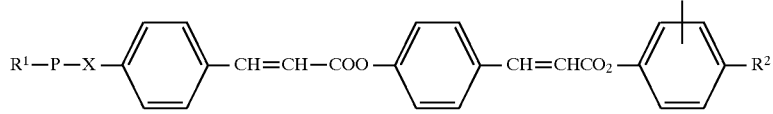   If

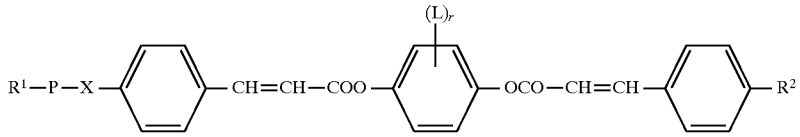   Ig

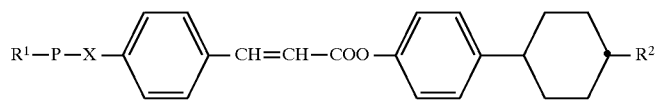   Ih

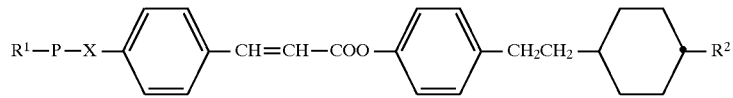   Ii wherein R¹, P, X and R² have the meaning given in claim 1, r is 0, 1 or 2, and L is halogen, nitro, cyano or an alkyl, alkoxy or alkanoyl group with 1 to 7 C atoms.

5. A reactive liquid crystalline compound according to claim 1, wherein R² independently has one of the meanings given for R¹—P—X—.

6. A reactive liquid crystalline compound according to claim 1, wherein at least one of the groups R² and P is a chiral group.

7. A polymerizable liquid crystalline mixture comprising at least one compound of the formula I as claim 1

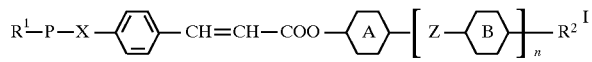

wherein

R¹ is $CH_2=CW-COO-$,

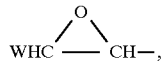

HWN—, $CH_2=CH_2$— or HS—$CH_2$—$(CH_2)_m$—COO— with W being H, Cl or alkyl with 1–5 C atoms and m being 1–7, P is alkylene with 1 to 12 C atoms, one or more non-adjacent $CH_2$ groups optionally being replaced by —O—, X is —O—, —S—, —CO—, —COO—, —OCO—, —C=C— or a single bond, R² is an optionally fluorinated alkyl radical with 1 to 15 C atoms, one or more $CH_2$ groups optionally being replaced by —O—, —S—, —CO—, —COO—, —OCO— or —O—CO—O— in such a manner that oxygen atoms are not linked directly to one another, or alternatively R² is halogen, cyano or has independently one of the meanings given for R¹—P—X—, Z is —$CH_2$—$CH_2$—, —COO—, —O—CO—, —CH=CH—COO—, —O—CO—CH=CH— or a single bond,

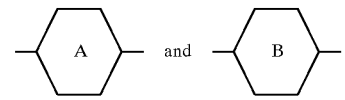

are each independently 1,4-phenylene or trans-1,4-cyclohexylene, the rings optionally being substituted by one or more alkyl, alkoxy or alkanoyl radicals with 1 to 7 C atoms, —CN, nitro or halogen atoms, and n is 0 or 1, and another liquid crystalline component.

8. An anisotropic polymer prepared by polymerization of a liquid crystalline mixture according to claim 7.

9. A linear or crosslinked polymer which contains at least one polymerized unit of a reactive liquid crystalline compound of the formula I as in claim 1:

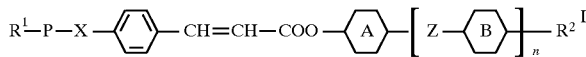

wherein

R¹ is $CH_2=CW-COO-$,

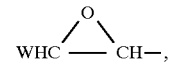

HWN—, $CH_2=CH_2$ or HS—$CH_2$—$(CH_2)_m$—COO— with W being H, Cl or alkyl with 1–5 C atoms and m being 1–7, P is alkylene with 1 to 12 C atoms, one or more non-adjacent $CH_2$ groups optionally being replaced by —O—, X is —O—, —S—, —CO—, —COO—, —OCO—, —C—C— or a single bond, R² is an optionally fluorinated alkyl radical with 1 to 15 C atoms, one or more $CH_2$ groups optionally being replaced by —O—, —S—, —CO—, —COO—, —OCO— or —O—CO—O— in such a manner that oxygen atoms are not linked directly to one another, or alternatively R² is halogen, cyano or has independently one of the meanings given for R¹—P—X—, Z is —$CH_2$—$CH_2$—, —COO—, —O—CO—, —CH=CH—COO—, —O—CO—CH=CH— or a single bond,

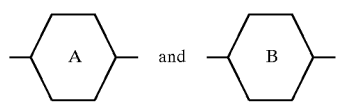

are each independently 1,4-phenylene or trans-1,4-cyclohexylene, the rings optionally being substituted by one or more alkyl, alkoxy or alkanoyl radicals with 1 to 7 C atoms, —CN, nitro or halogen atoms, and n is 0 or 1.

10. A decorative pigment, cosmetic, security application, or optical element which contains a polymer according to claim 9.

11. A polarizer film, retardation film, color filter, scattering display or adhesive which contains a polymer according to claim 9.

* * * * *